United States Patent [19]

Han

[11] Patent Number: 5,312,346
[45] Date of Patent: May 17, 1994

[54] NEEDLE REMOVING DEVICE

[75] Inventor: Sang I. Han, Northbrook, Ill.

[73] Assignee: Han Medical Designs, Inc., Northbrook, Ill.

[21] Appl. No.: 17,805

[22] Filed: Feb. 16, 1993

[51] Int. Cl.$^5$ .............................................. A61M 5/00
[52] U.S. Cl. ...................... 604/110; 604/263; 206/365; 206/366; 29/240
[58] Field of Search ........... 604/110, 192, 263; 128/919; 206/366, 365, 364, 363, 370; 29/240, 240.5

[56] References Cited

U.S. PATENT DOCUMENTS

| | | |
|---|---|---|
| 4,798,587 | 1/1989 | Willoughby . |
| 4,807,344 | 2/1989 | Kelson et al. . |
| 4,875,265 | 10/1989 | Yoshida .................................. 29/240 |
| 4,986,811 | 1/1991 | Thead et al. . |
| 4,989,307 | 2/1991 | Sharpe et al. ........................ 29/240 |
| 5,024,666 | 6/1991 | Pitach .................................. 604/263 |
| 5,067,223 | 11/1991 | Bruno . |
| 5,067,949 | 11/1991 | Freundlich et al. . |
| 5,069,667 | 12/1991 | Freundlich et al. . |
| 5,092,462 | 3/1992 | Sagstetler et al. ................... 206/366 |
| 5,127,522 | 7/1992 | Ranford ............................... 206/366 |
| 5,187,850 | 2/1993 | McCammon et al. ................. 29/235 |
| 5,188,598 | 2/1993 | Thead et al. ......................... 604/110 |

FOREIGN PATENT DOCUMENTS

| | | | |
|---|---|---|---|
| 0296406 | 12/1988 | European Pat. Off. ............ | 604/110 |
| 2205043 | 11/1988 | United Kingdom ................. | 604/110 |

Primary Examiner—C. Fred Rosenbaum
Assistant Examiner—Ronald K. Stright, Jr.
Attorney, Agent, or Firm—Baker & McKenzie

[57] ABSTRACT

An improved device for removing used needles from reusable syringes is provided. The device may be operated using only one hand and requires a single downward force applied to the syringe body by the health care worker. At the lower end of the downward stroke, the collar of the needle has been twisted off the syringe body and is automatically deposited into the receptacle for used needles. The health care worker releases the force and the apparatus automatically resets itself to receive another used needle. The device has few parts and may be assembled easily.

19 Claims, 2 Drawing Sheets

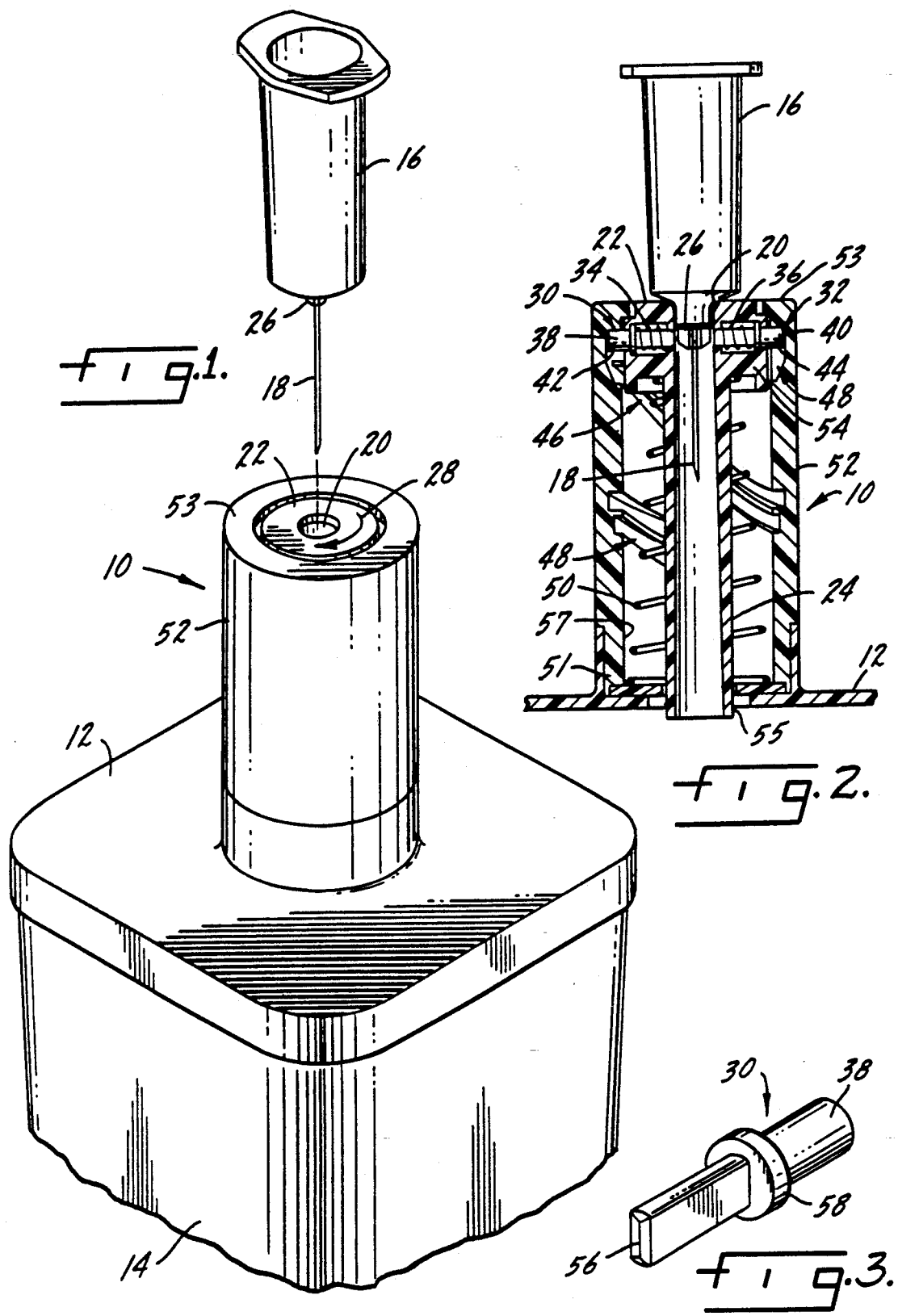

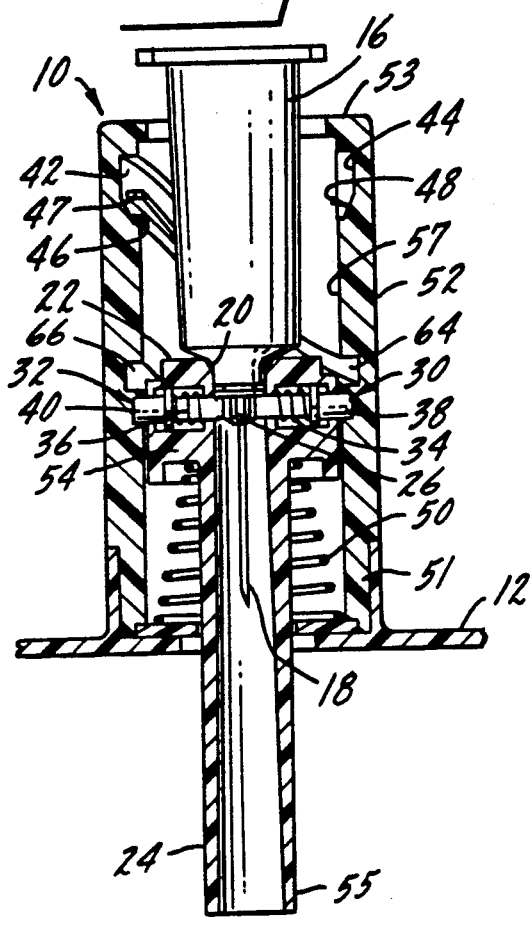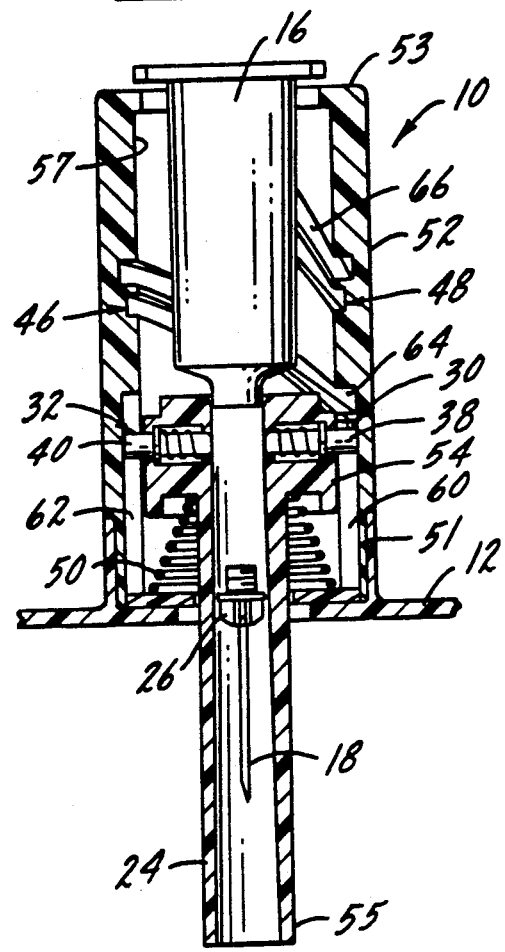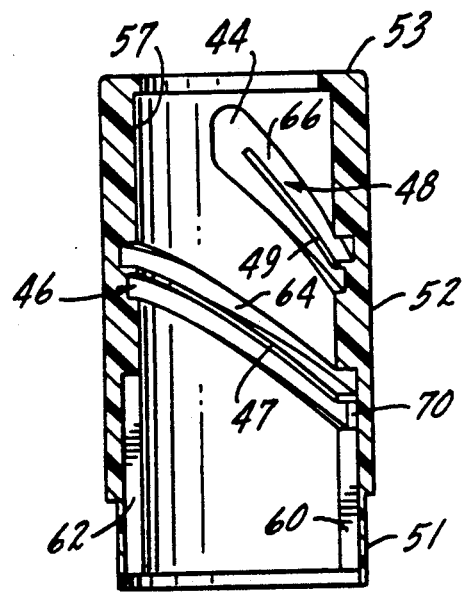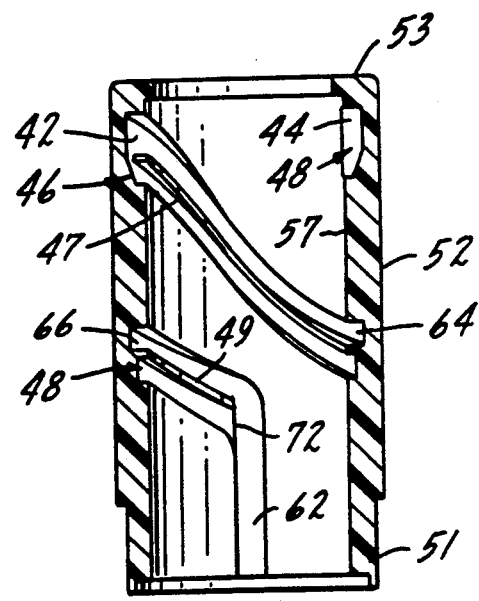

NEEDLE REMOVING DEVICE

FIELD OF THE INVENTION

This invention relates generally to needle-removing devices for safely removing used needles from reusable syringe bodies prior to disposal. More particularly, this invention relates to a needle-removing device that effectively removes a needle from a reusable syringe body with one easy downward motion that does not require the health care worker to manually handle the used needle.

BACKGROUND OF THE INVENTION

Devices have been developed for removing needles from reusable syringes, commonly sold under the trademark VACUTAINER, without exposing the health care worker to infectious diseases such as AIDS, hepatitis or syphilis. However, several problems are associated with the presently available needle-removing devices: some needle-removing devices include numerous parts and are difficult to assemble and manufacture; other needle-removing devices include complicated gear systems or employ electric motors and are therefore too expensive to manufacture; some needle-removing devices are entirely manual and therefore are slow to operate; and other needle-removing devices are too complicated to operate, are prone to operator error and are not considered to be effective safety devices. What is needed is a needle-removing device that is dependable, contains few parts, is easy to manufacture and is also easy and safe to operate.

The need for devices to remove needles from reusable syringe bodies without requiring the health care worker to handle the needle arose in the advent of infectious diseases, such as hepatitis, syphilis nd more recently, AIDS, which subject health care workers to serious risks in the workplace. Simply put, a health care worker may contract a serious infectious disease if a dirty needle, just used on an infected patient, mistakenly pricks the worker's skin thereby resulting in direct contact of the infected patient's bodily fluids with the bodily fluids of the worker. The inherent risk to health care workers created a demand for a device for removing needles from syringe bodies without requiring manual handling of the used needles by the workers thereby avoiding many accidental needle pricks to the hands of the workers.

One type of needle-removing device includes a slot for inserting the needle. The slot grips the collar of the needle and the user then rotates the syringe thereby removing the needle from the syringe body. The needle drops downward into a container. When the container is full, the used needles are discarded.

The problem associated with this type of device is that it requires multiple hand movements by the user. The user must first insert the needle in a relatively small slot, engage the collar of the needle in the slot and thereafter twist the syringe body an appropriate number of turns to effectively remove the needle from the syringe body. Often, the collars of the needles will get caught in the slot and then the workers must remove the needle from the slot by hand or employ an additional instrument. Further, if the worker leaves the used needle disposed in the slot, the needle and bodily fluid remained exposed.

A second type of design includes a device where the needle is inserted into a hole or slot and an internal gear mechanism causes the needle and collar to be twisted off the syringe body. The problem associated with these types of design is that they require numerous parts to manufacture and are difficult to assemble. Many of these types of designs require multiple drive gears that are prone to failure. Further, these types of devices are also expensive to manufacture.

A third type of design includes an electric motor driven device that grabs the needle as it is inserted into a slot. The motor drives the gears which twist the needle off the syringe body. These devices are ineffective because it includes numerous parts and is therefore more expensive to manufacture. Further, the device must be located near an electric outlet.

Thus, there is a present need for an effective removing device that is easy to manufacture as well as easy to operate. The present invention satisfies this need by providing an effective needle-removing device that can be manufactured from as little as eight parts. The device is actuated by simple downward movement of the needle and syringe by the worker. The needle is automatically removed from the syringe body and ejected into a receptacle below the needle-removing device and away from the worker.

BRIEF DESCRIPTION OF THE INVENTION

The present invention makes a significant contribution to the art of needle-removing devices by providing an improved needle-removing device that is easy to manufacture and easy to operate. The invention accomplishes this with a needle-removing device that can be assembled rom only a few parts and can be easily mounted to a container for receiving the used needles or to a table top with a container mounted therebelow for receiving the used needles.

The improved needle-removing device of the present invention includes a base member that is preferably cylindrical in configuration. The inner wall of the base member includes at least one helical slot and preferably two helical slots for accommodating the outer ends of pegs that grip and turn the collar of the needle. The helical slots include an upper end disposed near the upper end of the base member and a lower end disposed near the lower end of the base member. The upper and lower ends are of a first depth. The middle portion of the helical slot is of a second and shallower depth than the upper and lower ends of the helical slot. The transition from the deeper depth of the upper end of the slot to the shallower depth at the middle portion of the slot is gradual. The transition between the shallower depth at the middle portion of the slot to the deeper depth at the lower end of the slot is abrupt. Hence, there is an abrupt step at the lower end of the slot.

When the collar gripping peg is pushed downward from the deeper upper end of the helical slot into the shallower middle portion of the helical slot, the collar gripping peg is pushed inward thereby positively engaging the collar of the needle. The spiral helical path of the slot causes the peg and the collar to twist as the entire apparatus is pushed downward by the worker. When the collar gripping peg crosses the step at the lower end of the slot, the spring-biased peg is urged outward as it crosses the abrupt step that divides the shallow middle portion of the slot from the deeper lower end of the slot.

A tube is disposed within the base member, preferably along the axial center of the base member. The tube has an upper end that accommodates at least one, and preferably two collar gripping pegs that are spring biased outward and are accommodated in the upper ends of the helical slots when the apparatus is in the relaxed position. The collar gripping pegs are disposed approximately perpendicular to and directed toward the axial center of the base member. In the preferred embodiment, the tube is spring biased upward so that the upper end of the tube is disposed adjacent to the upper end of the base member in the relaxed position.

The apparatus is operated as follows. The worker, with one hand holding the syringe body, inserts the needle downward through the tube member disposed within the base. The worker grips the syringe body and pushes downward. Before the downward force is applied by the worker, the collar gripping pegs are disposed in the deeper upper ends of the helical slots and are spring biased outward toward the walls of the base member. As the worker pushes downward, the upper end of the tube and the collar gripping pegs are pushed downward and the pegs begin to enter the middle portions of the helical slots that are shallower thereby causing the collar gripping pegs to protrude inward towards the axial center of the base member and in a position to engage the collar of the needle. As the collar gripping pegs completely enter the middle portion of the helical slots, the pegs effectively grip the collar of the needle.

As the worker continues to push downward, the pegs, the tube and the needle follow the spiral/helical path of the helical slots. Because the worker is gripping the syringe body with one hand, the syringe body does not twist and the pegs begin to twist the collar and the needle off of the syringe body. By the time the tube, pegs, and the needle reach the lower ends of the helical slots, the collar of the needle has been rotated approximately 270° thereby resulting in the needle being twisted off of the syringe body. As the collar gripping pegs cross the step and enter into the lower end portion of the helical slot, the pegs are spring biased outward thereby releasing the now unscrewed collar of the needle and allowing the needle to drop downward through the lower end of the tube and into the needle receptacle.

The worker needs to push the syringe body down only once. Once the collar gripping pegs engage the lower ends of the helical slots at the bottom of the downward stroke, the needle is removed from the syringe body and received in the needle receptacle. The worker then releases the downward pressure on the syringe body and the tube and pegs proceed upward under the upward spring bias force imposed on the tube member to resume the ready position.

In the preferred embodiment, a return lane is provided in juxtaposition to each helical slot. The return lane and middle portion of the helical slot are separated by a wall and the return lane is connected to the upper and lower ends of the helical slot. The return lanes are of the same depth as the upper and lower ends of the helical slot. Therefore, at the bottom of the stroke, when the collar gripping pegs engage the lower ends of the helical slots, the pegs follow the path of the return lane upward to the relaxed position. The step at the lower end of the helical slot prevents the pegs from proceeding back up the helical slot.

The present invention also lends itself to an improved method for removing used needles from a syringe body. A worker, holding the syringe body, inserts a needle into the upper end of a tube disposed within a cylindrical base member. The worker pushes the syringe body, needle, and upper end of the tube downward until the tube reaches a bottom point within the base member.

Two spring biased pegs each initially engage an upper end of a helical slot. As the tube and pegs are pushed downward, the pegs enter into a shallower middle portion of the slot and protrude inward toward the needle collar. The pegs engage the collar and twist the needle off the syringe body as the pegs follow the helical slots downward toward the bottom of the base member. Upon arrival at the bottom of the base member, the needle is twisted off the syringe body and is released from the pegs as the pegs cross the steps disposed at the lower ends of the slots and protrude outward to engage the deeper lower ends of the helical slots.

At the bottom of the stroke, the worker releases the downward pressure on the apparatus and the spring biased tube and the pegs proceed upward. Return lanes are provided in a juxtaposition to the helical slots and are connected to the upper and lower ends of the helical slots. The pegs are blocked from re-entering the helical slots and, instead, follow the path of the return lanes and return in an upward movement and reach the relaxed position when they engage the upper ends of the helical slots. The apparatus is now ready to receive another needle.

It is therefore an object of the present invention to provide an improved needle-removing device that may be operated one-handed by a medical worker.

It is also an object of the present invention to provide an improved needle-removing device that may be manufactured from a minimum of parts to reduce manufacturing cost.

It is also an object of the present invention to provide an improved needle-removing device that is fast and easy to use.

Yet another object of the present invention is to provide an improved needle-removing device that may be mounted to a variety of used needle receptacles.

Another object of the present invention is to provide an improved method for removing used needles from reusable syringe bodies commonly known as VACUTAINERS.

BRIEF DESCRIPTION OF THE DRAWINGS

This invention is illustrated more or less diagrammatically in the accompanying drawings, wherein:

FIG. 1 is a perspective view of a needle, collar and syringe body being inserted into the upper end of a needle-removing device made in accordance with the present invention;

FIG. 2 is a front sectional view of the needle-removing device shown in FIG. 1 and further illustrating the needle, collar and syringe body inserted into the upper end of the device;

FIG. 3 is a perspective view of a collar gripping peg made in accordance with the present invention;

FIG. 4 is a front sectional view of the needle-removing device shown in FIG. 2, the syringe body and needle being partially pushed downward toward the lower end of the needle-removing device;

FIG. 5 is a front sectional view of the needle-removing device shown in FIG. 2, particularly illustrating the device pressed downward at the end of the downward stroke, the collar of the needle being released and the needle falls through toward the lower end of the tube;

FIG. 6 is a sectional view of the needle-removing device shown in FIG. 2, particularly illustrating the helical slots disposed in the inner wall of the base member; and FIG. 7 is another sectional view of the needle-removing device shown in FIG. 2, particularly illustrating the helical slots disposed in the inner wall of the base member.

DETAILED DESCRIPTION OF THE INVENTION

Like reference numerals will be used to refer to like or similar parts from Figure to Figure in the following description of the drawings.

The dramatic improvement contributed by the present invention is best understood after consideration of the complicated and intricate structures found in the prior art. Most conventional needle-removing devices require gears, cams, and perhaps electric motors to unscrew a needle from a syringe body. As shown in the Figures and further illustrated below, the present invention provides an improved needle-removing device that is both easy to use and easy to manufacture.

As seen in FIG. 1, an improved needle-removing apparatus 10 is mounted to the upper surface 12 of a disposable needle container 14. A worker inserts the reusable syringe body 16 with the attached needle 18 into the hole 20 in the upper surface 22 of the tube member 24 (see FIG. 2).

As will be seen below, as the worker pushes the syringe body 16 and the needle 18 downward, the entire tube member 24 rotates in the direction of the arrow 28 which causes the collar 26 of the needle 1 to be unscrewed from the syringe body 16.

Turning to FIG. 2, the syringe body 16 has engaged the upper surface 22 of the tube member 24 The collar 26 of the needle 18 is disposed adjacent to the collar gripping pegs 30, 32. The pegs 30, 32 are spring biased outward by springs 34, 36. The outer ends 38, 40 of the pegs 30, 32 are in abutting relationship with the upper ends 42, 44 of the helical slots, shown generally at 46, 48 respectively. The tube member 24, along with the pegs 30, 32 are spring biased upward toward the position illustrated in FIG. 2 by the spring 50. The tube member 24 is disposed within the base member 52, which is preferably cylindrical in configuration. The base member 52 may conveniently be mounted to a receptacle top 12.

FIG. 3 is an illustration of the peg 30 disposed within the upper end 54 of the tube 24 shown in FIG. 2 (peg 30 is identical to peg 32). The tapered inner end 56 engages the collar 2 of the needle 18. The outer end 38 engages the helical slot 46. The peripheral flange 58 engages the spring 34.

Turning to FIG. 4, a health care worker has partially inserted the syringe body 16 downward into the needle-removing device 10. The collar 26 is now partially unscrewed from the syringe body 16. This action has been caused by rotation of the pegs 30, 32 approximately 270° as they follow the path of the helical slots 46, 48 downward. The outer end 38 of the peg 30 has followed the path of the helical slot 46 and is now engaging a portion of the shallower middle portion of the slot 46 and is pushed inward toward the axial center of the base 52 and is positively engaging the collar 26. Similarly, the outer end 40 of the peg 32 has followed the path of the helical slot 48 and is now engaging the shallower middle portion of the helical slot 48 and is also positively engaging the collar 26 of the needle 18. It will be noted then the middle portions of the slots 46, 48 are shallower than the upper ends 42, 44 of the slots 46, 48 respectively and also the middle portions of the slots 46, 48 are shallower than the lower ends 60, 62 (see FIGS. 5 and 6) of the slots 46, 48 respectively.

Referring to FIGS. 4 through 7 collectively, as the pegs 30, 32 proceed down the slots 46, 48, the depth of the slots 46, 48 changes. The upper ends 42, 44 of the slots 46, 48 are relatively deep and the pegs 30, 32 are spring-biased outward and do not engage the collar 26 of the needle 18. The depth of the slots 46, 48 gradually decreases as the pegs 30, 32 proceed downward and the pegs 30, 32, now disposed in shallower middle portions of the slots 46, 48, are pushed inward so they engage the collar 26. At the lower ends 46, 48 of the slots 46, 48, the depth abruptly increases at the steps 70, 72 (see FIGS. 6 and 7) so that the pegs 30, 32 snap outward thereby disengaging the collar 26.

As seen in FIG. 5, when the syringe 16 is fully depressed within the apparatus 10, the outer ends 38, 40 of the pegs 30, 32 engage the outer ends 60, 62 of the slots 46, 48 and extend outward thereby releasing the now unscrewed collar 26 of the needle 18 from the syringe body 16. FIG. 5 is an illustration of the downstroke or the bottom end of the downward motion imparted by the worker. The spring 50 is fully compressed. At this point, when the worker releases the downward force on the syringe body 16, the spring 50 will push the tube member 4 upward towards the position shown in FIG. 2. The pegs 30, 32 will follow the path of the deeper return lanes shown at 64 and 66. It will be noted that the return lane 64 is of the same approximate depth as the upper end 42 of the helical slot 46. Similarly, the return lane 66 is of the same approximate depth as the upper end 44 of the helical slot 48. Thus, the pegs 30, 32 and tube member 24 proceed easily upward through the deeper return lanes and the entire tube member 24 quickly snaps back into the relaxed, upper position shown in FIG. 2 and the apparatus 10 is ready to receive a new needle 18 and syringe body 16.

For the purposes of clarification, it will be noted that the base member 52 includes an upper end 53 and a lower end 51. Similarly, the tube member 24 includes an upper end 54 and a lower end 55. The used needle 18 drops through the lower end 55 of the tube 24 before being received in the receptacle 14 (see FIG. 1). The spring biased pegs 30, 32 illustrated in FIGS. 2, 4 and 5 provide a means for engaging the collar 26. The helical slots 46, 48 disposed in the inner wall 57 of the base member 52 provide a means for twisting collar 26 upon the application of downward force on the syringe body 16.

FIGS. 6 and 7 illustrate the helical slots 46, 48. Turning to FIG. 6, the helical slot 48 begins at the upper end 44 which is deeper than the middle portion of the slot 48. The slot 48 terminates in the deeper lower end 62, which is of generally the same depth as the upper end 44. The depths abruptly change from shallow to deep at the steps indicated at 70, 72. The return lane 66 is also of generally the same depth as the upper end 44 and lower end 62. Turning to FIG. 7, the slot 46 begins with the deeper upper end 42 and terminates in the deeper lower end 64 shown in FIG. 6. The return lane 64 is of the same general depth as the upper end 42 and lower end 60 of the slot 46. The helical slot 48 is separated from the return lane 66 by a wall 49; the helical slot 46 is separated from the return lane 64 by a wall 47. The steps 70, 72 prevent the pegs 30, 32 from returning up the helical slots 46, 48 as opposed to the return lanes 64, 66.

An improved method for removing used needles 18 from the syringe body 16 is inherent from the present invention. The health care worker inserts the needle 18 into the hole 20 of the upper end 54 of the tube 24. The worker then presses downward on the syringe 16, still only using one hand, to force the tube member 24 downward through the base member 52. As the outer ends 38, 40 of the pegs 30, 32 enter the middle portions of the helical slots 46, 48, the pegs 30, 32 protrude inward to engage the collar 26. As the pegs 30, 32 follow the spiral path of the slots 46, 48, the pegs 30, 32 twist the collar 26 of the needle 18 of the syringe body 16, which is held in place by the worker. When the pegs 30, 32 reach the lower ends 60, 62 of the slots 46, 48 the collar 26 has been twisted off of the syringe body 16. The outer ends 38, 40 of the pegs 30, 32 have passed over the steps 70, 72 and have engaged the lower ends 60, 62 of the helical slots 46, 48 with an audible click which tells the worker that the downstroke has been completed. At this time, the pegs 30, 32 release the loosened collar 26 and the needle 18 falls downward through the lower end 55 of the tube member 24 into the container 14 disposed there below. The worker then simply removes the downward force applied to the syringe body 16 and the pegs 30, 32 proceed up the return lanes 64, 66 toward the position shown in FIG. 2. The apparatus 10 is now ready to remove another used needle 18 from a syringe body 16.

Although only one preferred embodiment of the present invention has been illustrated and described, it will at once be apparent to those skilled in the art that variations may be made within the spirit and scope of the invention. Accordingly, it is intended that the scope of the invention be limited solely by the scope of the hereafter appended claims and not by any specific wording and the foregoing description.

I claim:

1. An apparatus for removing a needle with a threaded collar from a syringe body, the needle being attached to the syringe body with the threaded collar, the apparatus comprising:

a base member having an upper end and a lower end,
   a tube member for receiving the needle, the tube member being disposed within the base member, means for moving the tube member upward and downward within the base member, the tube member including an upper end and a lower end,
   the upper end of the tube member including means for engaging the collar of the needle upon the application of a downward force on the syringe body when the needle is inserted into the upper end of the tube member,
   the base member including means for twisting the collar upon application of the downward force on the syringe body when the needle is inserted through the upper end of the tube member,
   the collar of the needle being twisted off the syringe body by the means for engaging and the means for twisting the collar upon arrival of the collar of the needle and upper end of the tube member at the lower end of the base member due to the application of the downward force on the syringe body.

2. The apparatus of claim 1,
   wherein the tube member is spring biased upward so that the upper end of the tube member is disposed within the upper end of the base member in ready position, the upper end of the tube member extending downward to the lower end of the base member upon application of downward force on the upper end of the tube member.

3. The apparatus of claim 2,
   wherein the spring bias of the tube member forces the tube member upward after the upper end of the tube member reaches the lower end of the base member and the downward force is released.

4. The apparatus of claim 3,
   wherein the means for engaging the collar of the needle includes at least two pegs disposed on opposing sides of the upper end of the tube member, the pegs being spring biased outward toward an inner wall in the base member.

5. The apparatus of claim 4,
   wherein the means for twisting the collar of the needle including at least two opposing helical slots disposed in the inner wall of the base member, each helical slot having an upper end, a lower end and a middle portion disposed therebetween, each middle portion being shallower than the upper and lower ends.

6. The apparatus of claim 5,
   wherein each peg having an inner end directed toward the tube member and an outer end disposed in one helical slot, each peg protruding inward to engage the collar of the needle when downwardly forced into the middle portion of one helical slot.

7. The apparatus of claim 6,
   wherein each helical slot is disposed adjacent to a return lane, each return lane being deeper than the portion of the helical slot disposed between the upper and lower ends of the helical slot, each return lane being connected to the upper and lower ends of one helical slot, the pegs following the return lanes as the pegs return to the upper ends of the helical slots from the lower ends of the helical slots under the upward spring bias force imposed on the tube member.

8. An apparatus for removing a needle from a syringe body, the needle being attached to the syringe body with a threaded collar, the apparatus comprising:

a base member, the base member having an axial center and including an inner wall, at least one helical slot disposed in the inner wall, the helical slot including an upper end and a lower end and a middle portion disposed therebetween, the upper end and lower end of the helical slot being deeper than middle portion disposed therebetween,
   a tube member disposed approximately along the axial center of the base member, means for moving the tube member upward and downward within the base member, the tube member having an upper end and a lower end, the upper end of the tube member including at least one peg disposed approximately perpendicular to and directed toward the axial center of the base member, the peg being spring biased in a radially outward direction, an outer end of the peg being accommodated in the helical slot, the tube member being spring biased upward, the outer end of the peg being disposed in the upper end of the helical slot when the upper end of the tube member is disposed within an upper end of the base member,
   the peg engaging the collar of the needle when the needle is pushed downward into the upper end of the tube member as the syringe engages the upper end of the tube member thereby forcing the outer end of the peg downward into the middle portion of the helical slot, the peg engaging the collar of the needle and twisting the needle as the peg and tube member follow the helical slot downward towards the lower end of the helical slot as the syringe and the needle are pushed downward, the peg twisting the collar of the needle, and the needle off the syringe body upon arrival of the peg at the lower end of the helical slot.

9. The apparatus of claim 8,
wherein, as the peg arrives at the lower end of the helical slot, the needle are separated from the syringe body and the peg disengages the collar of the needle as the outer end of the peg engages the lower end of the helical slot and the needle falls through the lower end of the tube member.

10. The apparatus of claim 8,
wherein the base member is mounted to the upper surface of a needle receptacle for receiving the needle as the needle passes through the lower end of the tube member.

11. The apparatus of claim 8,
wherein the helical slot is disposed adjacent to a return lane, the return lane being deeper than the middle portion of the helical slot, the return lane being connected to the upper and lower ends of a helical slot, the peg following the return lane as the peg returns to the upper end of the helical slot from the lower end of the helical slot under the upward spring bias force imposed on the tube member.

12. Tee apparatus of claim 8,
wherein the tube member is spring biased upward by a spring with an axial center, the tube member being disposed along the axial center of the spring.

13. The apparatus of claim 8,
whereby the base member includes two helical slots and two pegs, the pegs being disposed on opposing sides of the upper end of the tube member, the upper ends of the helical slots being disposed on opposing sides of the inner wall of the base member and the lower ends of the helical slots being disposed on opposing sides of the inner wall of the base member.

14. The apparatus of claim 13,
wherein, the needle is separated from the syringe body when the pegs arrive at the lower ends of the helical slots and the needle falls through the lower end of the tube member.

15. The apparatus of claim 13,
wherein each helical slot is disposed adjacent to a return lane, each return lane being deeper than the middle portion of the helical slot, each return lane being connected to the upper and lower end of a helical slot, the pegs following the return lanes as the pegs return to the upper ends of the helical slots from the lower ends of the helical slots under the upward spring bias force imposed on the tube member.

16. The apparatus of claim 13,
wherein the tube member is spring biased upward by a spring with an axial center, the tube member being disposed along the axial center of the spring.

17. The apparatus of claim 13,
wherein the base member is mounted to the upper surface of a needle receptacle for receiving the needle as the needle passes through the lower end of the tube member.

18. An apparatus for removing a needle from a syringe body, the needle being attached to the syringe body with a threaded collar, the apparatus comprising:

a base member, the base member having an axial center and including an inner wall, at least two helical slots disposed in the inner wall, each helical slot including an upper end and a lower end and a portion disposed therebetween, the upper end and lower ends of the helical slots being deeper than the middle portions disposed therebetween, the upper ends of the helical slots being disposed on opposing sides of the inner wall of the base member and the lower ends of the helical slots being disposed on opposing sides of the inner wall of the base member, a tube member disposed approximately along the axial center of the base member, means for moving the tube member upward and downward within the base member, the tube member having an upper end and a lower end, the upper end of the tube member including at least two pegs disposed approximately perpendicular to and directed toward the axial center of the base member, each peg being spring biased in a radially outward direction, an outer end of each peg being accommodated in one of the helical slots, the tube member being spring biased upward so that the outer ends of the pegs are disposed in the upper ends of the helical slots when the upper end of the tube member is disposed within an upper end of the base member, each peg engaging opposing sides of the collar of the needle when the needle is pushed downward into the upper end of the tube member as the syringe forcefully engages the upper end of the tube member thereby forcing the pegs downward into the middle portions of the helical slots, the pegs engaging the collar and twisting the collar as the pegs and tube member follow the helical slots toward the lower ends of the helical slots as the syringe and needle are pushed downward, the pegs twisting the collar of the needle off the syringe body upon arrival of the pegs at the lower ends of the helical slots, each helical slot being disposed adjacent to a return lane, each return lane being deeper than the portion of the helical slot disposed between the upper and lower ends of the helical slot, each return lane being connected to the upper and lower ends of a helical slot, the pegs following the return lanes as the pegs return to the upper ends of the helical slots from the lower ends of the helical slots under the upward spring bias force imposed on the tube member.

19. A method of removing a needle from a syringe body, the needle being attached to the syringe body with a threaded collar, the method comprising:

inserting the needle into an upper end of a tube member, the tube member being disposed within a base member, the base member having an axial center and including an inner wall, at least two helical slots disposed in the inner wall, each helical slot including an upper end and a lower end and a middle portion disposed therebetween, the upper end and lower ends of the helical slots being deeper than middle portions disposed therebetween, the upper ends of the helical slots being disposed on opposing sides of the inner wall of the base member and the lower ends of the helical slots being disposed on opposing sides of the inner wall of the base member, the tube member being disposed approximately along the axial center of the base member, the upper end of the tube member including at least two pegs disposed approximately perpendicular to and directed toward the axial center of the base member, each peg being spring biased in a radially outward direction, an outer end of each peg being accommodated in the helical slot, the tube member being spring biased upward so that the outer ends of the pegs are disposed in the upper ends of the helical slots when the upper end of the tube member is disposed within an upper end of the base member;

pressing the syringe body against an upper surface of the tube member and forcing the tube member, the needle and syringe body downward into the base member, each peg engaging opposing sides of the collar of the needle when the needle is pushed downward into the upper end of the tube member as the syringe engages the upper end of the tube member thereby forcing the pegs downward into the middle portions of the helical slots, the pegs engaging and twisting the collar of the needle as the pegs and the tube member follow the helical slots towards the lower ends of the helical slots as the syringe and needle are pushed downward, the pegs twisting the collar of the needle off the syringe body upon arrival of the pegs at the lower ends of the helical slots; and removing the downward force from the syringe body after the needle is twisted off the syringe body.

* * * * *